(12) United States Patent
Grossmann et al.

(10) Patent No.: US 6,512,123 B2
(45) Date of Patent: Jan. 28, 2003

(54) TRICYCLIC ALKYLHYDROXAMATE DERIVATIVES

(75) Inventors: Adelbert Grossmann, Eglfing (DE); Wolfgang von der Saal, Weinheim (DE); Tim Sattelkau, Mannheim (DE); Ulrich Tibes, Frankfurt (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/127,100

(22) Filed: Apr. 22, 2002

(65) Prior Publication Data

US 2002/0183513 A1 Dec. 5, 2002

(30) Foreign Application Priority Data

Apr. 23, 2001 (EP) .............................. 01109428

(51) Int. Cl.$^7$ .................... C07D 209/82; C07D 313/10; C07C 259/04
(52) U.S. Cl. ................. 548/444; 549/354; 562/621; 562/623
(58) Field of Search ..................... 548/444; 549/354; 562/621, 623

(56) References Cited

U.S. PATENT DOCUMENTS 5,369,108 A 11/1994 Breslow et al.

FOREIGN PATENT DOCUMENTS

| DE | 2208893 | 8/1973 |
|----|---------|--------|
| WO | WO 98/09934 | 3/1998 |
| WO | WO 98/55449 | 12/1998 |
| WO | WO 01/21583 | 3/2001 |

OTHER PUBLICATIONS

Hashimoto et al., Chemistry Letters, vol. 9, 1992, pp. 1639–1642.

Primary Examiner—Brian J. Davis
(74) Attorney, Agent, or Firm—George W. Johnston; Patricia S. Rocha-Tramaloni; Bernard Lau

(57) ABSTRACT

Compounds of formula I

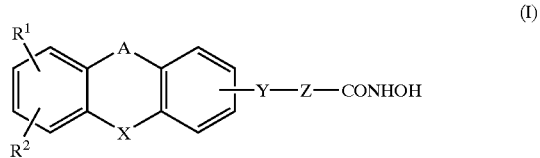

wherein R1, R2, A, X, Y and Z have the meanings provided in the specification, and their enantiomers, diastereoisomers, racemates, pharmaceutically acceptable salts and mixtures thereof. These compounds have HDAC inhibitory activity for inhibiting cell proliferation. Also provided is a process of manufacturing these compounds.

4 Claims, No Drawings

TRICYCLIC ALKYLHYDROXAMATE DERIVATIVES

BACKGROUND OF THE INVENTION

Transcriptional regulation is a major event in cell differentiation, proliferation, and apoptosis. Transcriptional activation of a set of genes determines cell destination and for this reason transcription is tightly regulated by a variety of factors. One of its regulatory mechanisms involved in the process is an alteration in the tertiary structure of DNA, which affects transcription by modulating the accessibility of transcription factors to their target DNA segments. Nucleosomal integrity is regulated by the acetylation status of the core histones. In a hypoacetylated state, nucleosomes are tightly compacted and thus are nonpermissive for transcription. They are relaxed by acetylation of the core histones, with the result being permissiveness to transcription. The acetylation status of the histones is governed by the balance of the activities of histone acetyl transferase (HAT) and histone deacetylase (HDAC). Recently, HDAC inhibitors have been found to arrest growth and apoptosis in several types of cancer cells, including colon cancer, T-cell lymphoma, and erythroleukemic cells. Given that apoptosis is a crucial factor in detecting cancer progression, HDAC inhibitors are promising reagents for cancer therapy as effective inducers of apoptosis (Koyama, Y., et al., Blood 96 (2000) 1490–1495).

Several structural classes of HDAC inhibitors have been identified and are reviewed in Marks, P. M., et al., Journal of the National Cancer Institute 92 (2000) 1210–1216. More specifically, WO 98/55449 (by The University of Queensland et al, "Hydroxamic Acid Compounds Having Anticancer And Anti-Parasitic Properties"), and U.S. Pat. No. 5,369,108 (by Breslow, R., et al., "Potent Inducers Of Terminal Differentiation And Methods Of Use Thereof") report alkanoyl hydroxamates with HDAC inhibitory activity.

We have now found that certain tricyclic alkylhydroxamate derivatives possess anti-cell-proliferation properties which are more potent than those in the aforementioned references. These properties are due to HDAC inhibition.

DESCRIPTION OF THE INVENTION

According to the invention there is provided a tricyclic alkylhydroxamate derivative of the formula I

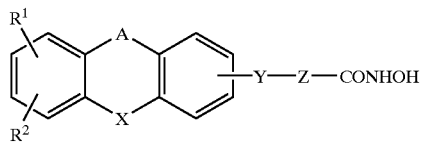

wherein
A denotes a bond, the groups —$CH_2$—O—, —$CH_2$—S—, —$CH_2$—$CH_2$-, or —NH—CO—;
X denotes the group —$NR^3$—, =CO, or —CH(OH,)—;
Y denotes an oxygen atom, a sulfur atom, or the group —$NR^4$—;
Z denotes a straight chain alkylene group comprising 4, 5, 6, 7, or 8 carbon atoms, wherein one $CH_2$ group may be replaced by an oxygen or a sulfur atom, or wherein 2 carbon atoms form a C=C double bond, and which is either unsubstituted or substituted by one or two substituents selected from (1–4C)alkyl and halogen atoms;
$R^1$ and $R^2$ denote substituents independently selected from a hydrogen atom, halogen atoms, (1–4C)alkyl, trifluoromethyl, hydroxy, (1–4C)alkoxy, benzyloxy, (1–3C)alkylenedioxy, nitro, amino, (1–4C)alkylamino, di[(1–4C)alkyl]-amino, or (1–4C)alkanoylamino groups;
$R^3$ and $R^4$ independently denote hydrogen atoms or (1–4C)alkyl groups;
their enantiomers, diastereoisomers, racemates, salts and mixtures thereof.

A suitable value for a substituent when it is a halogen atom is, for example, fluoro, chloro, bromo and iodo; when it is (1–4C)alkyl is, for example, methyl, ethyl, propyl, isopropyl, butyl, isobutyl, sec-butyl; when it is (1–4C)alkoxy is, for example, methoxy, ethoxy, propoxy, isopropoxy or butoxy; when it is (1–4C)alkylamino is, for example, methylamino, ethylamino or propylamino; when it is di-[(1–4C)alkyl]amino is, for example, dimethylamino, N-ethyl-N-methylamino, diethylamino, N-methyl-N-propylamino or dipropylamino; when it is (1–4C)alkanoylamino is, for example, formylamido, acetamido, propionamido or butyramido; and when it is (1–3C) alkylenedioxy is, for example, methylenedioxy, ethylenedioxy or propylenedioxy.

Preferred tricycles of formula I are dibenzoxepine, dibenzazepine, fluorene or carbazol.

Y is preferred an oxygen atom. Z is a straight chain alkylene group with 4 to 8 carbon atoms, preferably 4 to 7. The chain can be substituted by one or two halogen atoms, preferably chlorine, or a $C_1$-$C_4$-alkyl group, preferably methyl. One —$CH_2$-group of the chain can be replaced by an oxygen or sulfur atom, however, this group should not be the first or last member of the chain. A $CH_2$—$CH_2$-group of the chain can also form a —H=CH-group.

Preferred compounds of the invention include tricyclic alkylhydroxamate derivatives of the formula I

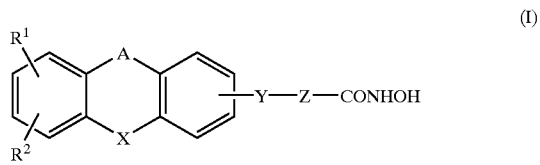

wherein
A denotes a bond, the groups —$CH_2$—O—, or —NH—CO—;
X denotes the group —$NR^3$—, =CO, or —CH(OH)—;
Y denotes an oxygen atom, a sulfur atom, or the group —$NR^4$—;
Z denotes a straight chain alkylene group comprising 4, 5, 6, 7, or 8 carbon atoms, wherein one $CH_2$ group may be replaced by an oxygen or a sulfur atom, or wherein 2 carbon atoms form a C=C double bond, and which is either unsubstituted or substituted by one or two substituents selected from (1–4C)alkyl and halogen atoms;
$R^1$ and $R^2$ denote substituents independently selected from halogen atoms, (1–4C)alkyl, trifluoromethyl, hydroxy, (1–4C)alkoxy, benzyloxy, (1–3C) alkylenedioxy, nitro, amino, (1–4C)alkylamino, di[(1–4C)alkyl]-amino, or (1–4C)alkanoylamino groups;
$R^3$ and $R^4$ independently denote hydrogen atoms or (1–4C)alkyl groups;
their enantiomers, diastereoisomers, racemates, salts and mixtures thereof.

Preparation of the Compounds of the Invention

A tricyclic alkylhydroxamate derivative of the formula I, or a pharmaceutically-acceptable salt thereof, may be prepared by any process known to be applicable to the preparation of chemically-related compounds. Such processes, when used to prepare a tricyclic alkylhydroxamate derivative of the formula I, or a pharmaceutically-acceptable salt thereof, are provided as a further feature of the invention and are illustrated by the following representative examples in which, unless otherwise stated, A, X, Y, Z, $R^1$, $R^2$, $R^3$, and $R^4$ have any of the meanings defined hereinbefore. The starting materials may be obtained by standard procedures of organic chemistry. The preparation of such starting materials is described within the accompanying non-limiting examples. Alternatively starting materials are obtainable by analogous procedures to those illustrated which are within the ordinary skills of an organic chemist.

a) One preferred method for the preparation of compounds of the formula I is the deprotection of compounds of the formula II

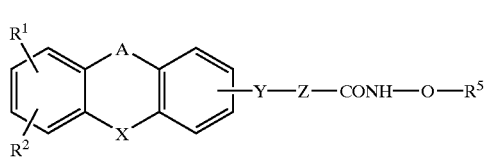

(II)

wherein $R^5$ is a suitable protecting group. Compounds of the formula II are new and included in the present invention.

Suitable protecting groups are the benzyl-, p-methoxybenzyl-, tert.butyloxy-ccarbonyl-, trityl-, or silyl groups such as the trimethylsilyl- or dimethyl-tert.butylsilyl-group. The reactions carried out depend on the type of the protecting group. When the protecting group is a benzyl- or p-methoxybenzyl group, the reaction carried out is a hydrogenolysis in an inert solvent such as an alcohol like methanol or ethanol, in the presence of a noble metal catalyst such as palladium on a suitable carrier such as carbon, barium sulfate, or barium carbonate, at ambient temperature and pressure. When the protecting group is the tert.butyloxycarbonyl-, trityl-, or a silyl group such as the trimethylsilyl- or dimethyl-tert.butylsilyl-group, the reaction is carried out in the presence of acids at a temperature between −20° C. and 60° C., preferably between 0° C., and ambient temperature. The acid may be a solution of hydrochloric acid in an inert solvent such as diethyl ether or dioxane, or trifluoro acetic acid in dichloromethane. Alternatively, when the protecting group is a silyl group such as the trimethylsilyl or dimethyl-tert.butylsilyl group, the reaction is carried out in the presence of a fluoride source such as sodium fluoride or tetrabutyl ammonium fluoride in an inert solvent such as dichloromethane.

Compounds of the formula II are obtained by the reaction of a tricyclic alkylhydroxamate of the formula III

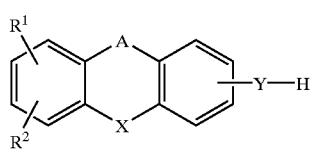

(III)

with a compound of formula IV

W—Z—CONH—O—$R^5$  (IV)

wherein W is a displaceable group and Z and $R^5$ have the meaning defined hereinbefore, in the absence or presence of a suitable base.

A suitable displaceable group W is, for example, a halogeno, or sulphonyloxy group, for example a chloro, bromo, methanesulphonyloxy or toluene-p-sulphonyloxy group. A suitable base is, for example, an organic amine base such as, for example, pyridine, 2,6-lutidine, collidine, 4-dimethylaminopyridine, triethylamine, morpholine, N-methyl-morpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

The reaction is conveniently carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran or 1,4-dioxane, an aromatic solvent such as toluene, or a dipolar aprotic solvent such as N,N-dimethylformamide, N,N-dimethyl-acetamide, N-methylpyrrolidin-2-one or dimethylsulfoxide. The reaction is conveniently carried out at a temperature in the range, for example, 10 to 250° C., preferably in the range 40–200° C.

The compounds of the general formula III are either commercially available or can be prepared according to the following literature references or in analogous manners. Compounds of the formula III wherein A denotes a bond and X denotes the group $NR^3$—, can be prepared according to the German Patent Application DE 2928483 (Lauer, K., and Kiegel, E.; Boehringer Mannheim GmbH). Compounds of the formula III wherein A denotes a bond, the group —$CH_2CH_2$—, or —$CH_2$—O— and X denotes the group =CO, can be prepared according to the German Patent Application DE 2208893 (Winter, W., et al.; Boehringer Mannheim GmbH).

Compounds of the formula IV are prepared by reacting compounds of formula W—Z—COOH (commercially available) with the compounds of the formula $H_2N$—O—$R^5$ (commercially available) wherein W, Z, and $R^5$ have the meaning defined hereinbefore. This is a two step reaction. In the first step, the carboxylate becomes activated. This reaction is carried out in an inert solvent or diluent, for example, in dichloromethane, dioxane, or tetrahydrofuran, in the presence of an activating agent. A suitable reactive derivative of an acid is, for example, an acyl halide, for example an acyl chloride formed by the reaction of the acid with an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester such as pentafluorophenyl trifluoroacetate or an alcohol such as methanol, ethanol, isopropanol, butanol or N-hydroxybenzotriazole; an acyl azide, for example an azide formed by the reaction of the acid and an azide such as diphenylphosphoryl azide; an acyl cyanide, for example a cyanide formed by the reaction of the acid and a cyanide such as diethylphosphoryl cyanide; or the product of the reaction of the acid and a carbodiimide such as dicyclohexylcarbodiimide. The reaction is carried out between −30° C. and 60° C., conveniently at or below 0° C. In the second step, hydroxylamine is added to the solution at the temperature used for the activation, and the temperature is slowly adjusted to ambient temperature.

b) Another preferred method for the preparation of compounds of the formula I involves the reaction of compounds of the formula V

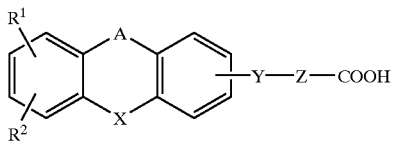

(V)

with hydroxylamine. This reaction typically involves a two-step one-pot procedure. In the first step, the carboxylate of the formula V becomes activated. This reaction is carried out in an inert solvent or diluent, for example, in dichloromethane, dioxane, or tetrahydrofuran, in the presence of an activating agent. A suitable reactive derivative of an acid is, for example, an acyl halide, for example an acyl chloride formed by the reaction of the acid with an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester such as pentafluorophenyl trifluoroacetate or an alcohol such as methanol, ethanol, isopropanol, butanol or N-hydroxybenzotriazole; an acyl azide, for example an azide formed by the reaction of the acid and an azide such as diphenylphosphoryl azide; an acyl cyanide, for example a cyanide formed by the reaction of the acid and a cyanide such as diethylphosphoryl cyanide; or the product of the reaction of the acid and a carbodiimide such as dicyclohexylcarbodiimide. The reaction is carried out between −30° C. and 60° C., conveniently at or below 0° C. In the second step, hydroxylamine is added to the solution, at the temperature used for the activation, and the temperature is slowly adjusted to ambient temperature.

Compounds of the formula V are prepared from compounds of the formula VI

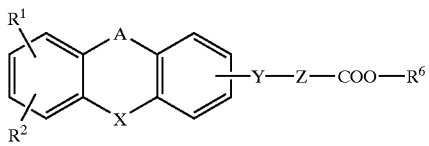

(VI)

wherein $R^6$ is an alkyl group, for example, a methyl, ethyl, or tert. butyl group or benzyl group, by hydrolysis. The conditions under which the hydrolysis is carried out depend on the nature of the group $R^6$. When $R^6$ is a methyl or ethyl group, the reaction is carried out in the presence of a base, for example, lithium hydroxide, sodium hydroxide, or potassium hydroxide in an inert solvent or diluent, for example, in methanol or ethanol. When $R^6$ is the tert.butyl group, the reaction is carried out in the presence of an acid, for example, a solution of hydrochloric acid in an inert solvent such as diethyl ether or dioxane, or trifluoro acetic acid in dichloromethane. When $R^6$ is the benzyl group, the reaction is carried out by hydrogenolysis in the presence of a noble metal catalyst such as palladium on a suitable carrier, such as carbon.

Compounds of the formula VI are prepared from compounds of the formula III

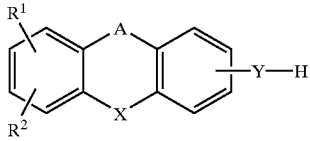

(III)

by reaction with compounds of the formula VII

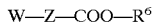

W—Z—COO—$R^6$ (VII)

in the presence of a suitable base.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

The reaction is conveniently carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran or 1,4-dioxane, an aromatic solvent such as toluene, or a dipolar aprotic solvent such as N,N-dimethylformamide, N,N-dimethylacetamide, N-methylpyrrolidin-2-one or dimethylsulfoxide. The reaction is conveniently carried out at a temperature in the range, for example, 10 to 250° C., preferably in the range 40–200° C.

Compounds of formula VII are commercially available.

c) A third preferred method for the production of compounds of the formula I involves the reaction of compounds of the formula VIII

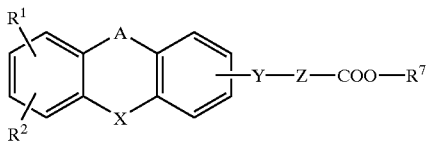

(VIII)

wherein $R^7$ is an (1–4C)alkyl group, for example, a methyl or ethyl group, with hydroxylamine in the presence of a suitable base.

The reaction is carried out in an inert solvent or diluent such as methanol or ethanol at temperatures between 0° C. and 100° C., conveniently at or near ambient temperature, and at a pH between 9 and 11. A suitable base is, for example, an alcoholate, for example, sodium methylate.

d) Those compounds of the formula I wherein one of the substituents is an amino group may be prepared by the reduction of a derivative of the formula I wherein the substituent is a nitro group. The reduction may conveniently be carried out by any of the many procedures known for such a transformation. The reduction may be carried out, for example, by the hydrogenation of a solution of the nitro compound in an inert solvent or diluent as defined hereinbefore in the presence of a suitable metal catalyst such as palladium or platinum. A further suitable reducing agent is, for example, an activated metal such as activated iron (produced by washing iron powder with a dilute solution of an acid such as hydrochloric acid). Thus, for example, the reduction maybe carried out by heating a mixture of the nitro compound and the activated metal in a suitable solvent or diluent such as a mixture of water and an alcohol, for example, methanol or ethanol, to a temperature in the range, for example, 50 to 150° C., conveniently at or near 70° C.

e) Those compounds of the formula I wherein X denotes the —CH(OH)— group maybe prepared by the reduction of a derivative of the formula I wherein X denotes the =CO group. The reduction may conveniently be carried out by any of the many procedures known for such a transformation. The reduction may be carried out, for example, by hydrogenation in an inert solvent or diluent as defined hereinbefore in the presence of a suitable metal catalyst such as palladium or platinum, for example, in methanol or ethanol, at a temperature in the range, for example, 0 to 1 00° C., conveniently at or near ambient temperature.

f) Those compounds of the formula I wherein one of the substituents is an (1–4C)alkanoylamino group, are prepared by acylation of a derivative of the formula I wherein the substituent is an amino group. A suitable acylating agent is, for example, any agent known in the art for the acylation of amino to acylamino, for example an acyl halide, for example an alkanoyl chloride or bromide, conveniently in the presence of a suitable base, as defined hereinbefore, an alkanoic acid anhydride or mixed anhydride, for example acetic anhydride or the mixed anhydride formed by the reaction of an alkanoic acid and an alkoxycarbonyl halide, for example an alkoxycarbonyl chloride, in the presence of a suitable base as defined hereinbefore. In general the acylation is carried out in a suitable inert solvent or diluent as defined hereinbefore and at a temperature, in the range, for example, –30 to 1 20° C., conveniently at or near ambient temperature.

Compounds of the formula VIII are prepared from a compound of the general formula III reacted with a compound of formula W—Z—COOR⁷, in like manner to the reaction of a compound of formula III with one of formula VII.

The enantiomers or diastereoisomers of the compounds of formula I can be obtained by usual methods as column chromatography or crystallization or optical resolution of enantiomers by treatment with optically active acids or bases or by using optically active starting materials.

"Pharmaceutically acceptable salts" refer to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e., a drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456–1457.

According to a further aspect of the invention there is provided a pharmaceutical composition which comprises a tricyclic alkylhydroxamate derivative of the formula I, or enantiomer, diastereoisomer, racemate, pharmaceutically-acceptable salt or mixture thereof, in association with a pharmaceutically-acceptable diluent or carrier. The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository. In general the above compositions may be prepared in a manner using conventional excipients. The tricyclic alkylhydroxamate will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a tricyclic alkylhydroxamate derivative of the formula I as defined hereinbefore for use in a method of treatment of the human or animal body by therapy. We have now found that the compounds of the present invention possess anti-cell-proliferation properties which are believed to arise from their histone deacetylase inhibitory activity. Accordingly the compounds of the present invention provide a method for treating the proliferation of malignant cells. Accordingly the compounds of the present invention are expected to be useful in the treatment of cancer by providing an anti-proliferative effect, particularly in the treatment of cancers of the breast, lung, colon, rectum, stomach, prostate, bladder, pancreas and ovary. It is in addition expected that a derivative of the present invention will possess activity against a range of leukemias, lymphoid malignancies and solid tumors such as carcinomas and sarcomas in tissues such as the liver, kidney, prostate and pancreas.

Thus according to this aspect of the invention there is provided the use of a tricyclic alkylhydroxamate derivative of the formula I, or a pharmaceutically-acceptable salt thereof, as defined hereinbefore in the manufacture of a medicament for use in the production of an anti-cell-proliferation effect in a warm-blooded animal such as man.

According to a further feature of this aspect of the invention there is provided a method for producing an anti-cell-proliferation effect in a warm-blooded animal, such as man, in need of such treatment which comprises administering to said animal an effective amount of a tricyclic alkylhydroxamate derivative as defined hereinbefore.

The anti-cell-proliferation treatment defined hereinbefore may be applied as a sole therapy or may involve, in addition to the compounds of the invention, one or more other anti-tumor substances, for example those selected from, for example, mitotic inhibitors, for example vinblastine; alkylating agents, for example cis-platin, carboplatin and cyclophosphamide; inhibitors of microtubule assembly, like paclitaxel or other taxanes; antimetabolites, for example 5-fluorouracil, capecitabine, cytosine arabinoside and hydroxyurea, or, for example, intercalating antibiotics, for example adriamycin and bleomycin; immunostimulants, for example trastuzumab; DNA synthesis inhibitors, e.g. gemcitabine; enzymes, for example asparaginase; topoisomerase inhibitors, for example etoposide; biological response modifiers, for example interferon; and anti-hormones, for example antioestrogens such as tamoxifen or, for example antiandrogens such as (4'-cyano-3-(4-fluorophenylsulphonyl)-2-hydroxy-2-methyl-3'-(trifluoromethyl) propionanilide, or other therapeutic agents and principles as described in, for example, Cancer: Principles & Practice of Oncology, Vincent T. DeVita, Jr., Samuel Hellmann, Steven A. Rosenberg; 5$^{th}$ Ed., Lippincott-Raven Publishers, 1997. Such conjoint treatment may be achieved by way of the simultaneous, sequential or separate dosing of individual components of the treatment. According to this aspect of the invention there is provided a pharmaceutical product comprising a tricyclic alkylhydroxamate derivative of the formula I as defined hereinbefore and an additional anti-tumor substance as defined hereinbefore for the conjoint treatment of cancer.

The invention will now be illustrated in the following non-limiting examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon or nitrogen;

(iii) column chromatography (by the flash procedure) and high pressure liquid chromatography (HPLC) were performed on Merck Kieselgel silica or Merck Lichroprep RP-18 reversed-phase silica obtained from E. Merck, Darmstadt, Germany;

(iv) yields are given for illustration only and are not necessarily the maximum attainable;

(v) melting points were determined using a Mettler SP62 automatic melting point apparatus, an oil-bath apparatus or a Kofler hot plate apparatus.

(vi) the structures of the end-products of the formula I were confirmed by nuclear (generally proton) magnetic resonance (NMR) and mass spectral techniques (Micromass Platform II machine using APCI or Micromass Platform ZMD using electrospray);

(vii) intermediates were not generally fully characterized and purity was assessed by thin layer chromatography.

EXAMPLE 1

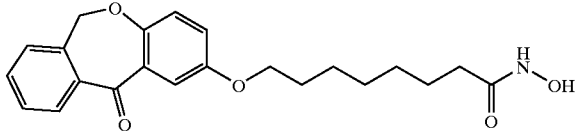

8-(11-Oxo-6,11-Dihydro-dibenzo[b,e]oxepin-2-yloxy)-octanoic Acid Hydroxyamide (a) In an ice bath, 14 ml triethylamine was added to a suspension of 3.2 g (20 mmol) O-benzylhydroxylamine hydrochloride in 150 ml dichloromethane. Stirring was continued until the solution became clear. Then, 4.5 g (20 mmol) omega-bromo octanoic acid was added, followed by 5.6 g (22 mmol) bis-(2-oxo-3-oxazolidinyl)-phosphorylchloride. Stirring was continued at ambient temperature for 18 h. The solution was extracted twice with 150 ml each of 1 M aqueous hydrochloric acid and twice with 150 ml each of 1 M aqueous sodium bicarbonate. The organic solvent was removed i. vac. to give 5.1 g (78%) of 8-bromo-octanoic acid benzyloxy-amide as a colorless oil. MS: 330 (M+H$^+$).

(b) 488 mg (3.5 mmol) Potassium carbonate was added to a solution of 400 mg (1.8 mmol) 2-hydroxy-6 H-dibenzo[b,e]oxepin-11-one and 580 mg (1.8 mmol) 8-bromo-octanoic acid benzyloxy-amide in dimethyl formamide. The slurry was heated to 100° C. for 1–4 h. After cooling to ambient temperature, water was added and extracted with ethyl acetate. The organic phase was washed with water, dried over sodium sulfate, filtered, and the solvent was evaporated. The residue was purified by column chromatography using ethyl acetate/heptane 1:1 as eluent. There was thus obtained 420 mg (50%)) 8-(11-Oxo-6,11-dihydro-dibenzo[b,e]oxepin-2-yloxy)-octanoic acid benzyloxyamide as a colorless oil. MS: 474 (M+H$^+$); 472 (M−H$^+$).

(c) 400 mg (0.845 mmol) 8-(11-Oxo-6,11-dihydro-dibenzo[b,e]oxepin-2 yloxy)-octanoic acid benzyloxyamide in 50 ml methanol was hydrogenated in the presence of palladium on calcium carbonate at ambient temperature and pressure. The catalyst was removed by filtration and the solvent was evaporated. The residue was purified by column chromatography (methanol/water 75:25). There was thus obtained 90 mg (28%) of the title compound as an amorphous solid. MS: 382 (M−H$^+$); 384 (M+H$^+$).

EXAMPLE 2

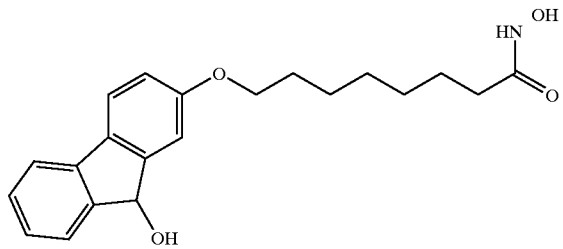

rac-8-(9-Hydroxy-9H-fluoren-2-yloxy)-octanoic Acid Hydroxyamide (a) In a manner analogous to that of example 1(b), 8-bromo-octanoic acid benzyloxy-amide (example 1(a); 0.3 g, 1.3 mmol) was reacted with 2-hydroxy-fluoren-9-one (0.30 g, 1.5 mmol) in the presence of potassium carbonate (0.21 g, 1.5 mmol) and dimethyl formamide (10 ml) to give 8-(9-oxo-9H-fluoren-2-yloxy)-octanoic acid benzyloxyamide as an almost colorless wax (yield 0.43 g, 63%; purified by column chromatography using silica gel and ethyl acetate: heptane=1:1 as eluent). MS (M−H$^+$)=442.

(b) In a manner anologous to that of example 1(c), 8-(9-oxo-9H-fluoren-2 yloxy)-octanoic acid benzyloxyamide (430 mg, 1 mmol) was hydrogenated to give the title compound (160 mg) in 46% yield as an amorphous solid. MS (M−H$^+$)=354.

EXAMPLE 3

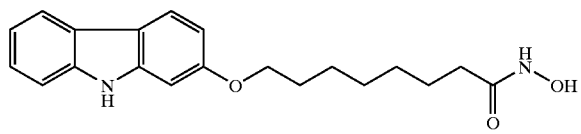

8-(9H-Carbazol-2-yloxy)-octanoic Acid Hydroxyamide (a) In a manner analogous to that of example 1(b), 8-bromo-octanoic acid benzyloxy-amide (example 1(a); 0.3 g, 1.1 mmol) was reacted with 2-hydroxy-9H-carbazol (0.3 g, 1.1 mmol) in the presence of potassium carbonate (0.15 g, 1.1 mmol) and DMF as solvent to give 8-(9H-carbazol-2-yloxy)-octanoic acid benzyloxyamide as an almost colorless wax (yield 0.1 g, 20%; purified by column chromatography using silica gel and ethyl acetate as eluent). MS (M+H$^+$)=483.

(b) In a manner anologous to that of example 1(c), 8-(9H-carbazol-2-yloxy)-octanoic acid benzyloxyamide (90 mg, 430 mmol) in tetrahydrofuran was hydrogenated in the presence of palladium on barium sulfate to give the title compound as a crystalline solid (16 mg). MS (M–H$^+$)=339.

EXAMPLE 4

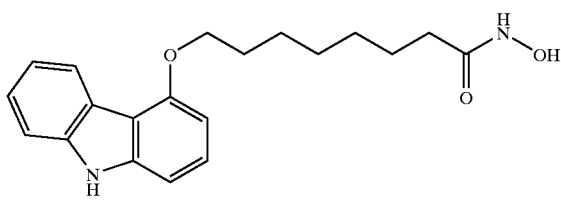

8-(9H-Carbazol-4-yloxy)-octanoic Acid Hydroxyamide (a) In a manner analogous to that of example 1(b), 8-bromo-octanoic acid benzyloxy-amide (example 1(a); 0.54 g, 1.6 mmol) was reacted with 4-hydroxycarbazol (0.3 g, 1.6 mmol) in the presence of potassium carbonate (0.23 g, 1.6 mmol) in dimethyl formamide to give 8-(9H-carbazol-4-yloxy)-octanoic acid benzyloxyamide as an almost colorless oil (yield 0.3 g, 42%; purified by column chromatography using silica gel and ethyl acetate: heptane 4: 6 as eluent). MS (M–H$^+$)=429.

(b) In a manner anologous to that of example 1(c), 8-(9H-Carbazol-4-yloxy)-octanoic acid benzyloxyamide (300 mg, 0.7 mmol) was hydrogenated in the presence of palladium on barium sulfate to give the title compound (110 mg) in 46% yield as an amorphous solid. MS (M–H$^+$)=339.

EXAMPLE 5

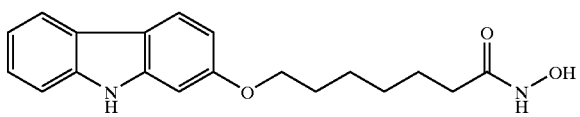

7-(9H-Carbazol-2-yloxy)-heptanoic Acid Hydroxyamide (a) In an ice bath, 2.4 ml triethylamine was added to a suspension of 2.7 g (17 mmol) O-benzylhydroxylamine hydrochloride in 100 ml dichloromethane. 3.6 g (17 mmol) 7-bromo heptanoic acid was added, followed by 5.3 g (21 mmol) bis-(2-oxo-3-oxazolidinyl)-phosphorylchloride Stirring was continued at ambient temperature for 18 h. The solution was extracted twice with 150 ml each of 1M aqueous hydrochloric acid and twice with 150 ml each of 1M aqueous sodium bicarbonate. The organic solvent was removed i. vac. and the residue was purified by column chromatography (silica gel; ethyl acetate: heptane 1:1) to give 1.55 g (30%) of 7-bromo-heptanoic acid benzyloxyamide as a colorless oil. MS: 314 (M+H$^+$).

(b) In a manner analogous to that of example 1 (b), 7-bromo-heptanoic acid benzyloxy-amide (1.8 g, 5.7 mmol) was reacted with 2-hydroxycarbazole (1.05 g, 5.7 mmol) in the presence of potassium carbonate (1.2 g, 8.6 mmol) in dimethyl formamide to give 7-(9H-carbazol-2-yloxy)-heptanoic acid benzyloxyamide as an almost colorless wax (yield 0.53 g, 22%; purified by column chromatography using silica gel and ethyl acetate: heptane 4:6 to 6:4 as an eluent). MS (M–H$^+$)=415.

(c) In a manner analogous to that of example 1 (c), 7-(9H-carbazol-2-yloxy)-heptanoic acid benzyloxyamide (530 mg, 1.3 mmol) was hydrogenated to give the title compound in 62% yield (260 mg) as a crystalline solid. mp 198° C. MS (M–H$^+$)=325.

EXAMPLE 6

6-(9H-Carbazol-2-yloxy)-hexanoic Acid Hydroxyamide

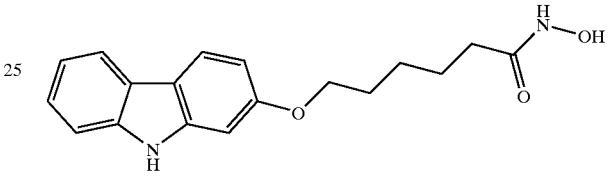

(a) 2-Hydroxycarbazole (0.5 g, 2.7 mmol), ethyl 6-bromohexanoate (0.6 g, 2.7 mmol), and potassium carbonate (0.4 g, 3.0 mmol) in dimethyl formamide (10 ml) were heated to 120° C. for 24 h. Water was added and extraction with ethyl acetate was performed. The combined organic phases were washed with water and dried (sodium sulfate). The solvent was removed i. vac. and the residue was purified by column chromatography (silica gel, ethyl acetate: heptane=1:1) to give ethyl 6-(9H-carbazol-2 yloxy)-hexanoate (290 mg, 33%) as a colorless solid. MS (M–H$^+$) 324.

(b) Ethyl 6-(9H-carbazol-2-yloxy)-hexanoate (270 mg, 0.8 mmol) and 1 N aqueous lithium hydroxide (2 ml, 2 mmol) in 15 ml methanol was heated to reflux for 1h. The solvent was removed, the residue was acidified by 1 ml 2N aqueous hydrochloric acid. The precipitate was collected to give 6-(9H-carbazol-2-yloxy)-hexanoic acid (230 mg, 93%) as a colorless solid. MS (M–H$^+$)296.

(c) 6-(9H-carbazol-2-yloxy)-hexanoic acid (220 mg, 0.74 mmol) in tetrahydrofuran (10 ml) was cooled to 0° C. Isobutyl chloroformiate (101 mg, 0.74 mmol) and N-methyl morpholine (112 mg, 1.1 mmol) was added and stirred at 0° C. for 15 min.

(d) Hydroxylamine hydrochloride (77 mg, 1.1 mmol) was added to a cold (0° C.) solution of potassium hydroxide (62 mg, 1.1 mmol) in methanol (2 ml). The precipitate was removed and the solution was added to a solution of the activated carboxylic acid (c). Stirring was continued for 1h at ambient temperature and the solvent was removed i.vac. The residue was purified by column chromatography (silica gel, ethal acetate: heptane 1:1) to give the title compound (53 mg, 23%) as a colorless solid. mp 192° C. MS (M–H$^+$) 311.

EXAMPLE 7

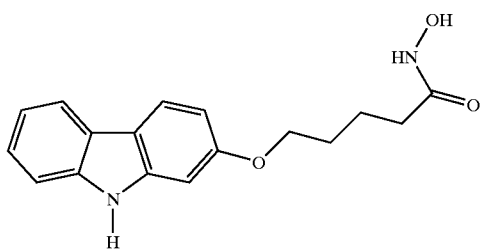

5-(9H-Carbazol-2-yloxy)-pentanoic Acid Hydroxyamide (a) In a manner analogous to that of example 6(a), ethyl 5-bromo-pentanoate (685 mg, 3.28 mmol) was reacted with 2-hydroxycarbazole (600 mg, 3.28 mmol) to give ethyl 5-(9H-carbazol-2-yloxy)-pentanoate (350 mg, 34%) as a colorless solid. MS (MH$^+$)310.

(b) In a manner analogous to that of example 6(b), ethyl 5-(9H-carbazol-2 yloxy)-pentanoate (400 mg, 1.3 mmol) was saponified to give 5-(9H-carbazol-2-yloxy)-pentanoic acid (350 mg, 96%) as a colorless solid. MS (M–H$^+$)282.

(c) In a manner analogous to that of example 6(c), 5-(9H-carbazol-2-yloxy)-pentanoic acid (350 mg, 1.2 mmol) was converted to the title compound to give 130 mg (30%) as colorless solid (MS (M–H$^+$)297.

EXAMPLE 8

In an analogous manner to that described in the examples 1–7 the following compounds are prepared:

(a) 7-(9H-Carbazol-4-yloxy)-heptanoic acid hydroxyamide (b) 7-(9H-Carbazol-3-yloxy)-heptanoic acid hydroxyamide (c) 7-(9H-Carbazol-1-yloxy)-heptanoic acid hydroxyamide (d) 7-(9-Methyl-carbazol-2-yloxy)-heptanoic acid hydroxyamide (e) 7-(9H-carbazol-2-yloxy)-5-methyl-heptanoic acid hydroxyamide (f) 7-(9H-carbazol-2-yloxy)-4-methyl-heptanoic acid hydroxyamide (g) 7-(9H-carbazol-2-yloxy)-3-methyl-heptanoic acid hydroxyamide (h) 7-(9H-carbazol-2-yloxy)-2-methyl-heptanoic acid hydroxyamide (i) 8-(9H-carbazol-2-yloxy)-2-methyl-octanoic acid hydroxyamide (j) 7-(9H-carbazol-2-yloxy)-4-oxa-heptanoic acid hydroxyamide (k) 7-(9H-carbazol-2-yloxy)-3-methyl-4-oxa-heptanoic acid hydroxyamide (l) 7-(9H-carbazol-2-yloxy)-3-oxa-heptanoic acid hydroxyamide (m) 7-(9H-carbazol-2-yloxy)-3-oxa-5cis-heptenoic acid hydroxyamide (n) 7-(9H-carbazol-2-yloxy)-3-oxa-5trans-heptenoic acid hydroxyamide (o) 7-(9H-carbazol-2-yloxy)-2-methyl-3-oxa-heptanoic acid hydroxyamide

EXAMPLE 9

Evaluation of Inhibitory Properties of the Compounds of the Invention

To measure the inhibitory properties of the compounds of the invention, a screening assay was performed using an aminocoumarin derivative of an omega-acetylated lysine as substrate for the enzmye. This assay has been described in detail in the literature (Hoffmann, K., et al., Nucleic Acids Res. 27 (1999)2057–2058). Using the protocol described therein, there was measured the inhibitory effect of the compounds at a concentration of 10 nM. The observed inhibition rates for selected compounds are shown in the following table:

| Title compound of example No. | Inhibitory effect at 10 nM in % |
|---|---|
| 1 | 62 |
| 2 | 79 |
| 3 | 86 |
| 4 | 97 |
| 5 | 100 |
| 6 | 80 |
| 7 | 69 |

In the same assay, suberanilohydroxamic acid (SAHA), which was included as a reference, showed an inhibitory effect of 42% at 10 nM.

What is claimed is:

1. At least one compound selected from a compound of formula I

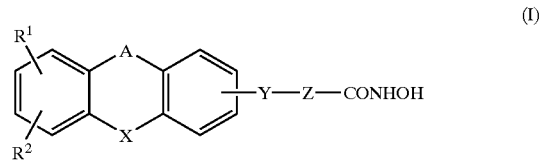

(I)

wherein

A denotes a bond, or is selected from —CH$_2$—O—, —CH$_2$—S—, —CH$_2$—CH$_2$—, and —NH—CO—;

X denotes the group —NR$^3$—, =CO, or —CH(OH$_1$)—;

Y denotes an oxygen atom, a sulfur atom, or the group —NR$^4$—;

Z denotes a straight chain alkylene group selected from 4, 5, 6, 7, and 8 carbon atoms, wherein one CH$_2$ group may be replaced by an oxygen or a sulfur atom, or wherein 2 carbon atoms form a C=C double bond, and which is optionally substituted by one or two substituents selected from (1–4C)alkyl and halogen atoms;

R$^1$ and R$^2$ denote substituents independently selected from a hydrogen atom, halogen atoms, (1–4C)alkyl, trifluoromethyl, hydroxy, (1–4C)alkoxy, benzyloxy, (1–3C)alkylenedioxy, nitro, amino, (1–4C)alkylamino, di[(1–4C)alkyl]-amino, and (1–4C)alkanoylamino groups;

R$^3$ and R$^4$ independently denote hydrogen atoms or (1–4C)alkyl groups;

and its enantiomers, diastereoisomers, racemates, pharmaceutically acceptable salts and mixtures thereof.

2. The at least one compound of formula I according to claim 1 wherein

A denotes a bond, or is selected from —CH$_1$—O— and —NH—CO—;

X denotes the group —NR$^3$—, =CO, or —CH(OH)—;
Y denotes an oxygen atom, a sulfur atom, or the group —NR$^4$—;
Z denotes a straight chain alkylene group selected from 4, 5, 6, 7, or 8 carbon atoms, wherein one CH$_2$ group may be replaced by an oxygen or a sulfur atom, or wherein 2 carbon atoms form a C=C double bond, and which is optionally substituted by one or two substituents selected from (1–4C)alkyl and halogen atoms;
R$^1$ and R$^2$ denote substituents independently selected from halogen atoms, (1–4C)alkyl, trifluoromethyl, hydroxy, (1–4C)alkoxy, benzyloxy, (1–3C)alkylenedioxy, nitro, amino, (1–4C)alkylamino, di[(1–4C)alkyl]-amino, and (1–4C)alkanoylamino groups;
R$^3$ and R$^4$ independently denote hydrogen atoms or (1–4C)alkyl groups;
and its enantiomers, diastereoisomers, racemates, pharmaceutically acceptable salts and mixtures thereof.

3. The at least one compound of formula I according to claim 1 selected from the group of
8-(11-Oxo-6,11-dihydro-dibenzo[b,e]oxepin-2-yloxy)-octanoic acid hydroxyamide, rac-8-(9-Hydroxy-9H-fluoren-2-yloxy)-octanoic acid hydroxyamide,
8-(9H-Carbazol-2-yloxy)-octanoic acid hydroxyamide,
8-(9H-Carbazol-4-yloxy)-octanoic acid hydroxyamide,
7-(9H-Carbazol-2-yloxy)-heptanoic acid hydroxyamide,
6-(9H-Carbazol-2-yloxy)-hexanoic acid hydroxyamide, and
5-(9H-Carbazol-2-yloxy)-pentanoic acid hydroxyamide.

4. A process for making a compound of formula I

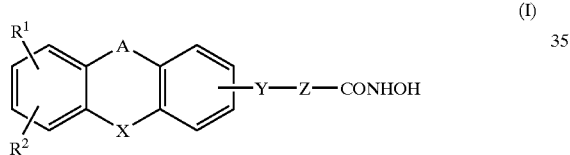
(I)

wherein
A denotes a bond, or is selected from —CH$_2$—O—, —CH$_2$—S—, —CH$_2$—CH$_2$—, and —NH—CO—;
X denotes the group —NR$^3$—, =CO, or —CH(OH$_1$)—;
Y denotes an oxygen atom, a sulfur atom, or the group —NR$^4$—;
Z denotes a straight chain alkylene group selected from 4, 5, 6, 7, and 8 carbon atoms, wherein one CH$_2$ group may be replaced by an oxygen or a sulfur atom, or wherein 2 carbon atoms form a C=C double bond, and which is optionally substituted by one or two substituents selected from (1–4C)alkyl and halogen atoms;
R$^1$ and R$^2$ denote substituents independently selected from a hydrogen atom, halogen atoms, (1–4C)alkyl, trifluoromethyl, hydroxy, (1–4C)alkoxy, benzyloxy, (1–3C)alkylenedioxy, nitro, amino, (1–4C)alkylamino, di[(1–4C)alkyl]-amino, and (1–4C)alkanoylamino groups;
R$^3$ and R$^4$ independently denote hydrogen atoms or (1–4C)alkyl groups;
by reacting a compound of formula III

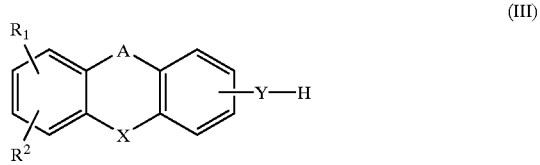
(III)

a) with a compound of formula IV

W—Z—CONH—O—R$^5$ (IV)

wherein
W is a displaceable group and R$^5$ is a protecting group, to obtain a compound of formula II

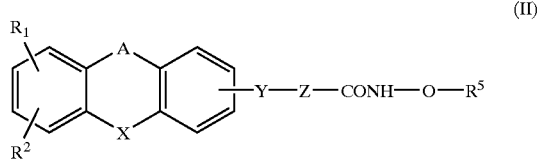
(II)

whereafter R$^5$ is split off, or
b) with a compound of formula VII

W—Z—COO—R$^6$ (VII)

wherein
R$^6$ is an alkyl or benzyl group, in the presence of a base, to obtain a compound of formula VI

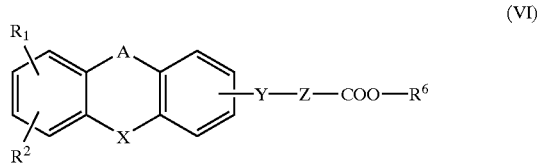
(VI)

and hydrolysis of the compound of formula VI and reaction with hydroxylamine, to obtain a compound of formula I.

* * * * *

UNITED STATES PATENT AND TRADEMARK OFFICE
CERTIFICATE OF CORRECTION

PATENT NO. : 6,512,123 B2
DATED : January 28, 2003
INVENTOR(S) : Adelbert Grossmann et al.

It is certified that error appears in the above-identified patent and that said Letters Patent is hereby corrected as shown below:

<u>Column 14,</u>
Line 44, delete "or -CH(OH$_1$)-;" and insert -- or -CH(OH)-; --
Line 66, delete "-CH$_1$-O- and" and insert -- -CH$_2$-O- and --

<u>Column 15,</u>
Line 45, delete "or-CH(OH$_1$)-;" and insert -- or -CH(OH)-;" --

Signed and Sealed this

Twelfth Day of August, 2003

JAMES E. ROGAN
*Director of the United States Patent and Trademark Office*